(12) United States Patent
Coppeta

(10) Patent No.: US 7,327,453 B2
(45) Date of Patent: Feb. 5, 2008

(54) POST DISPERSION SPATIALLY FILTERED RAMAN SPECTROMETER

(75) Inventor: David A. Coppeta, Atkinson, NH (US)

(73) Assignee: Axsun Technologies, Inc., Billerica, MA (US)

(*) Notice: Subject to any disclaimer, the term of this patent is extended or adjusted under 35 U.S.C. 154(b) by 30 days.

(21) Appl. No.: 11/383,410

(22) Filed: May 15, 2006

(65) Prior Publication Data
US 2006/0256329 A1 Nov. 16, 2006

Related U.S. Application Data

(60) Provisional application No. 60/680,878, filed on May 13, 2005.

(51) Int. Cl.
*G01J 3/44* (2006.01)
*G01N 21/65* (2006.01)

(52) U.S. Cl. ..................................................... 356/301

(58) Field of Classification Search .................. 356/301
See application file for complete search history.

(56) References Cited

U.S. PATENT DOCUMENTS 3,622,243 A * 11/1971 Wada .......................... 356/301

* cited by examiner

*Primary Examiner*—F. L. Evans
(74) *Attorney, Agent, or Firm*—Houston Eliseeva LLP

(57) ABSTRACT

To achieve a given spectral resolution with reduced detector size and commercially available pixel pitches, the Raman spectrum is shifted across the detector array such as by one of the following methods: 1) tuning the excitation wavelength; 2) rotating the grating; 3) displacing the effective input slit (fiber) and acquiring the spectrum under stepped displacement conditions; and 4) displacement of a lens relative to input fiber to displace effective input slit relative to the detector. A composite spectrum is formed and deconvolution of the entrance aperture image and/or pixel masking is then used.

20 Claims, 2 Drawing Sheets

POST DISPERSION SPATIALLY FILTERED RAMAN SPECTROMETER

RELATED APPLICATIONS

This claims the benefit of U.S. Provisional Application No. 60/680,878, filed May 13, 2005, which is incorporated herein by reference in its entirety.

BACKGROUND OF THE INVENTION

Conventional Raman spectrometers use a fixed wavelength laser source and a notch filter on the return path to block the source wavelength but allow the Stokes-shifted wavelengths to pass. A dispersive element is used to then to spatially disperse the Raman response. A multi-element detector is used to detect the dispersed Raman spectra. The size of detector is selected so that it provides enough elements (pixels) such that each pixel provides one wavelength resolution element.

In these conventional systems, resolution is generally limited by the entrance slit as it is imaged onto the detector and thus convolves the spectrum. The physical size of the detector's active area and the spatial dispersion (product of angular dispersion and lens focal length) set the range of spectrometer wavelength coverage. Decreasing the pixel size increases spectral resolution up to the limit imposed by the entrance slit. Alternatively for fixed pixel size, resolution may be increased by increasing detector size and spatial dispersion. Unfortunately, with increases in size, the detector array becomes more costly, especially for non-silicon detectors. The optics also becomes more difficult to design and more costly due to the increased field requirement at a fixed numerical aperture.

There are three principal problems with conventional Raman spectrometers.

The first is the size of the detector, grating, and optics. This leads to an instrument that is physically large—typically too large for a handheld configuration.

The second problem, for spectrometers that use multiple detector elements to increase speed of measurement, is the cost of the detector array. A non-silicon detector with many pixels is expensive. Since many materials fluoresce when illuminated with source wavelengths in the visible or short wavelength infrared (IR), it is preferable to excite Raman samples with a near infrared source. This pushes the Raman, Stokes-shifted spectrum into the near IR (NIR) as well, forcing the use of detector materials such as InGaAs. The cost of InGaAs arrays is high, with the driving cost parameter being the area of InGaAs in the array. Thus anything that can be done to reduce the length of InGaAs required to detect the spectrum can provide significant cost advantages.

Finally, the third problem is that for non-silicon based detector arrays the smallest commercially available pixel size is often limited. In the case of InGaAs, the smallest available pixel pitch is currently limited to 25 micrometers ($\mu$m) and thus forces long arrays for high resolution.

Recently, an alternate approach has been proposed in U.S. Pat. Appl. Publ. No. 2005/0264808 A1, which is incorporated herein by this reference, and demonstrated. It uses a multi-order filter, such as an etalon of finesse N, which only allows certain discrete narrow bands of wavelengths (of a periodic nature) to pass. By tuning the excitation laser or the etalon, the Raman spectrum is swept through these N pass bands (filter orders) and detected on the multi-element detector. This technique eliminates the entrance slit and pixel limitations on resolution provided that the orders are well separated on the detector. Full separation limits how small the detector area can be for a given number of orders, entrance slit width, and multi-order filter characteristic.

The multi-order filter Raman system provides the multiplex advantage while simultaneously providing a fine spectral resolution governed by the multi-order filter's transmission characteristics. The spacing required between orders to keep crosstalk to an acceptable level dictates the length of the InGaAs array for any fixed number of orders N (fixed multiplex advantage).

SUMMARY OF THE INVENTION

The present invention seeks to further reduce the size and cost of the detector, and the spectrometer, by removing the restriction of discrete orders physically spaced from one another.

The present invention is directed techniques to achieve a given spectral resolution with reduced detector size and commercially available pixel pitches. Assuming one starts with a conventional spectrometer, the detector pixel size in concert with the entrance slit limit spectral resolution. Decreasing the detector pixel size increases resolution until the size of the pixel approaches the image size of the entrance slit. Decreasing the pixel size further has rapidly diminishing returns on resolution. On the other hand, decreasing the size of the entrance slit will improve spectral resolution until the image of the slit approaches the detector pixel size and then further reduction yields diminishing return. In the case of reducing the entrance slit, input power is reduced, which is undesirable for a Raman spectrometer that is typically light starved. In either case, the detector pixel size for commercially available InGaAs detectors is limited to 25 $\mu$um or greater, which bounds the achievable resolution.

The current invention seeks to reduce the limitation of commercially available detectors by one of two methods. Both methods rely on shifting the Raman spectrum across the detector array such as by one of the following methods: 1) tuning the excitation wavelength; 2) rotating the grating; 3) displacing the effective input slit (fiber) and acquiring the spectrum under stepped displacement conditions; and 4) displacement of a lens relative to input fiber to displace effective input slit relative to the detector. The Raman spectra are acquired under stepped displacement conditions In general according to one aspect, the invention features a method for detecting a Raman spectrum. The method comprises illuminating a sample with an excitation signal, detecting Raman spectral responses of the sample with a detector system, such as a single element detector or a detector array, through an aperture while shifting a Raman spectra relative to the detector system, combining the Raman spectral responses into a composite spectrum, and deconvolving an image of the aperture on the detector system from the composite spectrum.

In different embodiments, the step of detecting the Raman spectral responses while shifting the Raman spectra comprises tuning a wavelength of the excitation signal, tuning a dispersive element; shifting an aperture relative to the detector array; and/or shifting an optical train relative to the detector array.

In general according to one aspect, the invention features a system for detecting a Raman spectrum. This system has a controller for receiving spectral data from the detector array while shifting Raman spectra relative to the detector array, combining the Raman spectral responses into a composite response, and deconvolving an image of the aperture on the detector array from the composite response.

In general according to other aspects, the invention features method or system that use a masked detector array to reduce an effective pixel size of pixels in a detector array, while shifting a Raman spectra relative to the detector array and The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
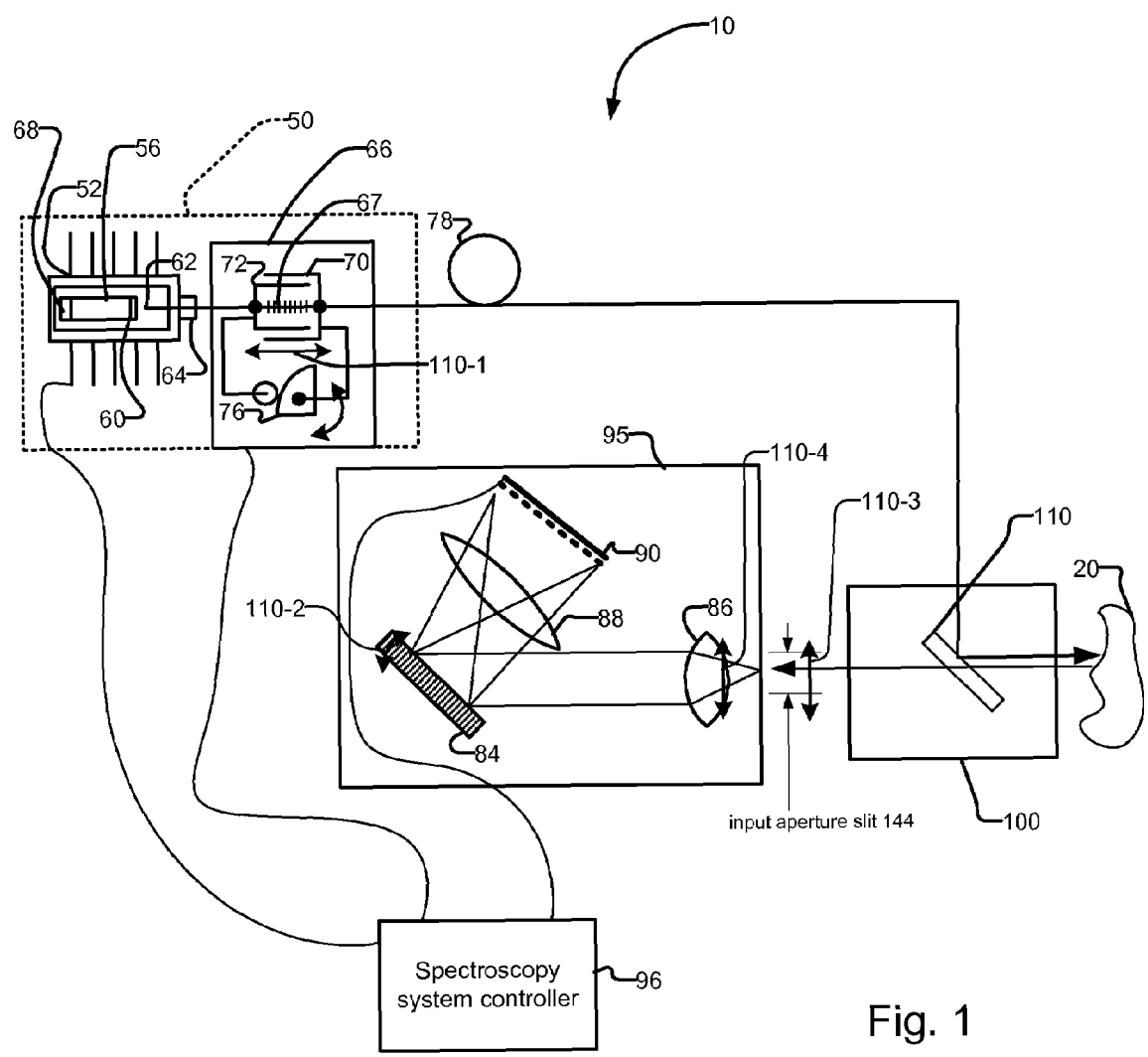
FIG. 1 is a schematic view showing a Raman spectroscopy system according to the present invention.

FIG. 1 shows a Raman spectroscopy system 10, which has been constructed according to the principles of the present invention.

This embodiment takes the multiple low-resolution spectra that differ in the fact that each low-resolution spectrum is shifted with respect to one another on the array. One of the follow methods is preferably used: 1) tuning the excitation wavelength; 2) rotating the grating; 3) displacing the effective input slit (fiber) and acquiring the spectrum under stepped displacement conditions; and 4) displacement of a lens relative to input fiber to displace effective input slit relative to the detector Specifically, the spectroscopy system comprises a semiconductor tunable laser subsystem 50. The tunable laser subsystem 50 comprises a semiconductor diode module 52. In the illustrated example, this module 52 is a hermetic package such as a butterfly hermetic package. The diode laser module 52 holds a semiconductor gain element 56. In the present embodiment, this gain element 56 is a semiconductor optical amplifier, and specifically, a reflective semiconductor optical amplifier. The semiconductor reflective optical amplifier 56 preferably comprises a reflective back facet 68 and an antireflection coated (AR) coated front facet 60. This class of device is useful in the construction of external cavity tunable semiconductor lasers.

In the illustrated embodiment, the external cavity tunable laser configuration provided by a wavelength tunable element module 66, which provides tunable narrow band feedback into the semiconductor gain element 56. In the preferred embodiment, this is a Bragg grating tuning system. Specifically, it comprises a fiber Bragg grating 67 that is mechanically stretched by a stretcher system. Specifically, a first half of the stretcher 70 and a second half of the stretcher 72 are moved toward and away from each other in the direction of arrow 110-1. In the current embodiment, a cam system 76 is used in order to mechanically stretch the fiber Bragg grating 67.

An optical fiber pigtail 78 transmits the excitation signal from the semiconductor tunable laser subsystem 50 to a probe subsystem 100. The light from the semiconductor chip 56 is coupled into the fiber pigtail 78 via a facet 62. This fiber goes through the hermetic package 52 via a fiber feedthrough 64 in one example.

In the preferred embodiment, the fiber pigtail 78 is polarization controlling fiber that controls the polarization of the light transmitted through it. Specifically, polarization controlling fiber is used between the gain element 56 and the grating 67 and between the grating and the probe subsystem 100. In the preferred embodiment, it is polarization maintaining fiber, although other polarization controlling systems could be used such as polarization stripping systems or polarizing fiber.

The probe subsystem 100 couples the tunable excitation signal from the tunable laser subsystem 50 to the sample 20 and collects light from the sample 20. A notch filter system 110 is used to separate the excitation signal from the Raman response in one embodiment.

The spectroscopy subsystem 95 detects and resolves the spectrum of the light returning from the sample 20.

The light from the sample 20 is received through an aperture slit 144. The light is collimated by a lens 86 and directed onto a dispersive element. In the preferred embodiment, a reflective grating 84 is used. Although gratings and hologram dispersive elements are used in other embodiments. Second lens 88 is used to image the spectrum and the aperature onto the array detector 90.

According to the invention, one or more techniques are used to shift the Raman spectrum relative to and over the length of the detector array 90.

In a preferred embodiment, the tunable laser 50 is used. Specifically, wavelength tuning is accomplished in one embodiment by changing the length, see arrow 110-1, of the fiber grating 67. This changes the wavelength of the excitation signal, thus changing or shifting the Raman spectrum.

In another embodiment, the grating dispersive element 84 is tilted, see arrow 110-2. This shifts the spectrum on the detector array 90.

In another embodiment, the input position, see arrow 110-3, of the input aperture or slit 144 is shifted relative to the detector 90.

In still another embodiment, the lens 86 of the spectrometer optical train is shifted, see arrow 110-4.

Figure 2:
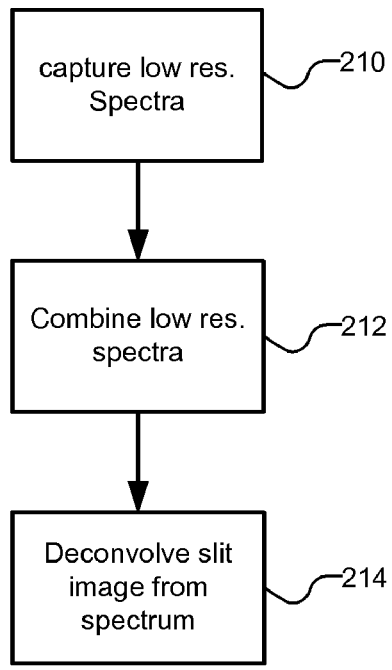
FIG. 2 is a flow diagram illustrating the inventive method.

FIG. 2 illustrates the process for using the shifted spectra to obtain a higher resolution Raman spectra.

In step 210, low-resolution spectra are captured for different shifts between the spectra and the detector array 90 by the controller 96 that controls the tunable laser 50 for example while reading out spectral data from the detector array 90. Specifically the spectra are captured for different excitation wavelengths (see reference 110-1), different tilt angles for the grating (see reference 110-2), or different positions for the aperture (see reference 110-3) or lens (see reference 110-4).

In step 212, the low resolution spectra are combined into a composite, high resolution spectrum through an appropriate super-resolution technique by controller 96. This is similar in concept to the way synthetic aperture radar images are formed from multiple low-resolution images. Super-resolution extracts sub-pixel information from the varied low-resolution images to achieve an image with an "effective" pixel size that is much smaller than the physical detector pixel size.

The advantage of this super resolution approach is that no additional filters are required. Nonetheless, it should be noted that the entrance slit may still limit resolution depending on size. In this case, assuming the high-resolution "effective" pixels are sufficiently small to meet the Nyquist sampling criteria Then in step 214, the spectrometer entrance slit image on the detector array 90 is deconvolved from the composite high-resolution spectral image by the controller 96.

The ability to perform this deconvolution relies on a known slit function in which illumination is uniform, as well as spectrometer optics with a sufficiently flat field. This embodiment incurs no extra loss.

In one modification, a single element detector is used in place of the detector array 90. This requires more spectral shifting over the detector to obtain the desired spectral width. In one example, a widely tunable laser is used as the tunable excitation source 50. This widely tunable source tunes over the spectral width of the required Raman spectra.

Figure 3:
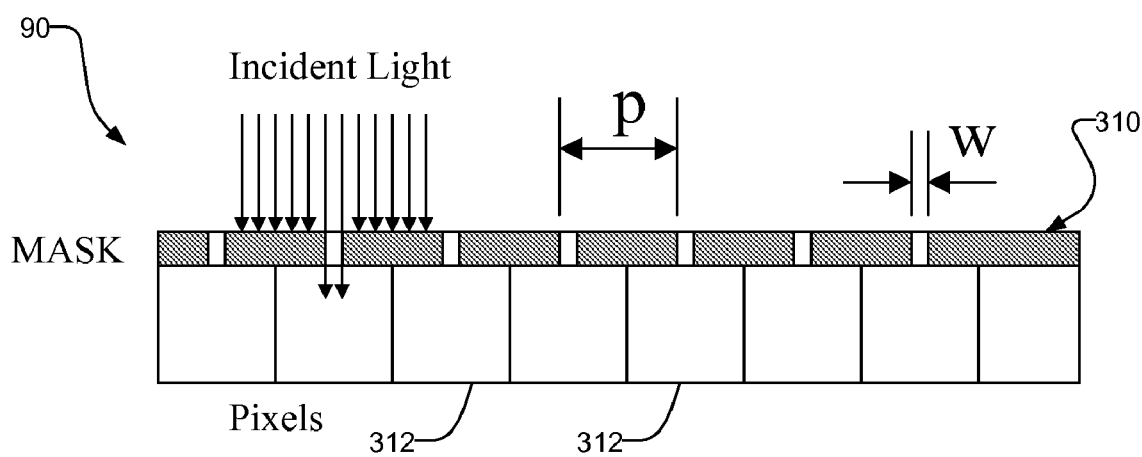
FIG. 3 shows a masked detector array according to a second embodiment of the invention.

FIG. 3 illustrates a configuration of the detector array 90 used in a second embodiment of the present invention. This embodiment avoids the need to perform the deconvolution step.

The second embodiment achieves the effective resolution by masking the detector array 90 itself using a physical aperture mask 310. The aperture mask has the same pitch, p, as the detector elements 312 but the transmission width, w, is equal to the desired effective pixel size.

The pattern, or mask, 310 is preferably aligned precisely during the fabrication of the detector array 90. The transmission width is roughly centered on a pixel of the array. In this way, each detector pixel 312 responds to light from one and only one mask window whose width is the desired effective pixel size. This eliminates detector pixel crosstalk and if the mask is made by photolithographic techniques, it will approximate an ideal rectangle sampling function.

Then, the multiple spectra sampled with this mask 310 are preferably combined directly to achieve an equivalent high-resolution image whose effective pixel size is the mask transmission window width.

Note that the spectra should be stepped or shifted by the mask transmission window width by one of the above-mentioned shifting techniques, see 110-1, 110-2, 110-3, 110-4.

As in the first embodiment, deconvolution with the entrance slit image can be performed if required provided the Nyquist sampling is satisfied and the optics are sufficiently flat field. Alternatively, if the input slit is sufficiently narrow, no deconvolution is required, provided the mask can be fabricated with sufficiently narrow slit width w to achieve the desired resolution. This allows the minimum detector area to be realized, i.e., that for which the spectral resolution element is no larger than the smallest required to achieve the target SNR requirement. The penalty for this small size is that the mask only allows a small fraction of the incident light to strike a detector pixel. Due to the convolution of the spectrum with the image of the entrance slit, this corresponds to an extra insertion loss. The magnitude of the loss is estimated as $IL=10*\log(w/(\text{Slit Image}))$.

For either embodiment, the total spectrum shift required in the low-resolution images is equal to the pitch of the detector pixels. The advantages include the reduction of the physical size, and thus cost, of the detector, which is often the most expensive element in the system. The physical mask more easily and precisely defines the filter function, and the alignment and assembly operation is easier. Finally the physical size of the system is reduced since the detector itself is smaller and the required dispersion is smaller.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting a Raman spectrum, the method comprising:
    illuminating a sample with an excitation signal;
    detecting Raman spectral responses of the sample with a detector system through an aperture while shifting a Raman spectra relative to the detector system;
    combining the Raman spectral responses into a composite spectrum; and
    deconvolving an image of the aperture on the detector array from the composite spectrum.

2. A method as claimed in claim 1, wherein the step of detecting the Raman spectral responses while shifting the Raman spectra comprises tuning a wavelength of the excitation signal.

3. A method as claimed in claim 1, wherein the step of detecting the Raman spectral responses while shifting the Raman spectra comprises tuning a dispersive element.

4. A method as claimed in claim 1, wherein the step of detecting the Raman spectral responses while shifting the Raman spectra comprises shifting the aperture relative to the detector system.

5. A method as claimed in claim 1, wherein the step of detecting the Raman spectral responses while shifting the Raman spectra comprises shifting an optical train relative to the detector system.

6. A system for detecting a Raman spectrum, the system comprising:
    an excitation source for illuminating a sample with an excitation signal;
    a spectrometer for detecting Raman spectral responses of the sample, the spectrometer comprising an aperture for receiving light from the sample, a detector array for detecting the Raman spectral responses, and a dispersive element for dispersing the Raman spectral responses over the detector array;
    a controller for receiving spectral data from the detector array while shifting a Raman spectra relative to the detector array, combining the Raman spectral responses into a composite response, and deconvolving an image of the aperture on the detector array from the composite response.

7. A system as claimed in claim 6, wherein the excitation source is a tunable source for generating a tunable excitation signal for shifting the Raman spectra relative to the detector array.

8. A system as claimed in claim 6, wherein the dispersive element is tuned to shift the Raman spectra relative to the detector array.

9. A system as claimed in claim 6, wherein the aperture is shifted relative to the detector array to shift the Raman spectra relative to the detector array.

10. A system as claimed in claim 6, wherein an optical train of the spectrometer is shifted relative to the detector array to shift the Raman spectra relative to the detector array.

11. A method for detecting a Raman spectrum, the method comprising:

masking a detector array to reduce an effective pixel size of pixels in a detector array;

illuminating a sample with an excitation signal;

detecting Raman spectral responses of the sample with the detector array while shifting a Raman spectra relative to the detector array; and combining the Raman spectral responses into a composite spectrum.

12. A method as claimed in claim 11, wherein the step of detecting the Raman spectral responses while shifting the Raman spectra comprises tuning a wavelength of the excitation signal.

13. A method as claimed in claim 11, wherein the step of detecting the Raman spectral responses while shifting the Raman spectra comprises tuning a dispersive element.

14. A method as claimed in claim 11, wherein the step of detecting the Raman spectral responses while shifting the Raman spectra comprises shifting an aperture relative to the detector array.

15. A method as claimed in claim 11, wherein the step of detecting the Raman spectral responses while shifting the Raman spectra comprises shifting an optical train relative to the detector array.

16. A system for detecting a Raman spectrum, the system comprising:

an excitation source for illuminating a sample with an excitation signal;

a spectrometer for detecting Raman spectral responses of the sample, the spectrometer comprising a detector array for detecting the Raman spectral responses, a mask for reducing an effective pixel size of pixels in the detector array, and a dispersive element for dispersing the Raman spectral responses over the detector array; and a controller for receiving spectral data from the detector array while shifting a Raman spectra relative to the detector array, and combining the spectral responses into a composite response.

17. A system as claimed in claim 16, wherein the excitation source is a tunable source for generating a tunable excitation signal for shifting the Raman spectra relative to the detector array.

18. A system as claimed in claim 16, wherein the dispersive element is tuned to shift the Raman spectra relative to the detector array.

19. A system as claimed in claim 16, wherein an aperture is shifted relative to the detector array to shift the Raman spectra relative to the detector array.

20. A system as claimed in claim 16, wherein an optical train of the spectrometer is shifted relative to the detector array to shift the Raman spectra relative to the detector array.

* * * * *